(12) United States Patent
Goldberg et al.

(10) Patent No.: US 6,706,780 B2
(45) Date of Patent: *Mar. 16, 2004

(54) METHOD OF AND COMPOSITION FOR PREVENTING TISSUE DAMAGE

(75) Inventors: Eugene P. Goldberg, Gainesville, FL (US); James W. Burns, Holliston, MA (US)

(73) Assignee: University of Florida, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/759,166

(22) Filed: Jan. 16, 2001

(65) Prior Publication Data

US 2003/0208281 A1 Nov. 6, 2003

Related U.S. Application Data

(63) Continuation of application No. 08/485,832, filed on Jun. 7, 1995, now abandoned, which is a division of application No. 08/141,017, filed on Oct. 26, 1993, now abandoned, which is a continuation-in-part of application No. 08/026,125, filed on Mar. 3, 1993, now Pat. No. 5,350,573, which is a continuation of application No. 07/818,125, filed on Jan. 8, 1992, now abandoned, which is a division of application No. 07/696,960, filed on May 8, 1991, now Pat. No. 5,140,016, which is a continuation of application No. 07/555,377, filed on Jul. 19, 1990, now Pat. No. 5,080,893, which is a continuation of application No. 07/199,687, filed on May 31, 1988, now abandoned.

(51) Int. Cl.$^7$ .................................................. A61F 2/00
(52) U.S. Cl. ...................... 523/113; 427/2.1; 623/23.72
(58) Field of Search ........................... 623/11.11, 23.72; 424/78.18; 427/2.1, 2.24, 2.25, 2.3; 523/113

(56) References Cited

U.S. PATENT DOCUMENTS

| | | | | |
|---|---|---|---|---|
| 4,100,309 A | * | 7/1978 | Micklus et al. ................ 427/2 |
| 4,375,461 A | * | 3/1983 | Gander et al. ................ 424/56 |
| 4,585,666 A | * | 4/1986 | Lambert ........................ 427/2 |
| 4,589,873 A | * | 5/1986 | Schwartz et al. ............. 427/2 |
| 4,657,820 A | | 4/1987 | Halpern et al. |
| 4,722,867 A | * | 2/1988 | Halpern et al. .......... 428/476.6 |
| 4,776,853 A | | 10/1988 | Klement et al. |
| 4,784,990 A | | 11/1988 | Nimrod et al. |
| 4,801,475 A | * | 1/1989 | Halpern et al. ................ 427/3 |
| 4,806,382 A | * | 2/1989 | Goldberg et al. ............. 427/2 |

(List continued on next page.)

OTHER PUBLICATIONS

Davis et al., Surgery, vol. 2, p. 87 (1937).
Gozalez, Surgery, vol. 26, p. 181 (1949).

(List continued on next page.)

*Primary Examiner*—David H. Willse
*Assistant Examiner*—Javier G. Blanco
(74) *Attorney, Agent, or Firm*—Miles & Stockbridge P.C.; Dennis P. Clarke

(57) ABSTRACT

An improved method and composition for preventing damage to tissue and/or organs during surgery and during harvesting, implanting, manufacture and manipulation of bioprostheses therefrom. Tissue surfaces and surgical articles involved in the surgery and bioprostheses are coated with a solution of a hydrophilic, polymeric material prior to manipulation of the tissue and/or organs during surgery. The composition comprises a solution of a polymeric material having a molecular weight of about 50,000 D or above having a concentration of from about 0.01% to about 15% by weight.

14 Claims, 1 Drawing Sheet

ABRASIVE TISSUE DAMAGE PROTECTION BY HA SOLUTIONS

U.S. PATENT DOCUMENTS

| | | | | | |
|---|---|---|---|---|---|
| 4,819,617 | A | * | 4/1989 | Goldberg et al. | 128/897 |
| 4,835,003 | A | * | 5/1989 | Becker et al. | 427/2 |
| 4,902,289 | A | | 2/1990 | Yannis | |
| 4,979,959 | A | | 12/1990 | Guire | |
| 5,080,893 | A | | 1/1992 | Goldberg et al. | |
| 5,140,016 | A | | 8/1992 | Goldberg et al. | |
| 5,350,573 | A | | 9/1994 | Goldberg et al. | |
| 5,632,979 | A | | 5/1997 | Goldberg et al. | |
| 6,010,692 | A | | 1/2000 | Goldberg et al. | |
| 6,238,799 | B1 | * | 5/2001 | Opolski | 428/423.1 |
| 6,387,450 | B1 | * | 5/2002 | Shah et al. | 427/385.5 |

OTHER PUBLICATIONS

Hunter et al., J. Bone Joint Surg., vol. 53A, p. 829 (1971).
Ellis, Surg. Gynecol. Obst., vol. 133, pp. 197–511 (1971).
Lindsay et al., In Verdan, C. (ed). Tendon Surgery of the Hand, Lond, Churchill Livingstone, pp. 35–39 (1979).
Potenza, J. Bone Joint Surg., vol. 45A, p. 1217 91963).
Verdan, J. Bone Joint Surg., vol. 54A, p. 472 (1972).
St. Onge et al., Clin. Orthop., vol. 148, pp. 259–275 (1980).
Thomas et al., Clin. Orthop., vol. 206, pp. 281–289 (May, 1986).
Weiss et al., Bull. Hosp. Jt. Dis. Orthop. Inst., vol. 46(1), pp. 9–15 (1986).
Goldberg et al., Arch. Surg., vol. 115, pp. 776–780 (1980).
Berquist et al. Eur. Surg. Res., vol. 9, p. 321 (1977).
Neuwirth et al., Am. J. Obstet. Gynecol., vol. 121, p. 420 (1974).
Hadick et al., Military Medicine, vol. 152, p. 144 (1987).

* cited by examiner

METHOD OF AND COMPOSITION FOR PREVENTING TISSUE DAMAGE

This is a continuation of application Ser. No. 08/485,832 filed Jun. 7, 1995 now abandoned, which is a divisional of Ser. No. 08/141,017 filed Oct. 26, 1993 now abandoned, which is a continuation-in-part of Ser. No. 08/026,125 filed Mar. 3, 1993 (now U.S. Pat. No. 5,350,573), which is a continuation of Ser. No. 07/818,125 filed Jan. 8, 1992 now abandoned, which is a divisional of Ser. No. 07/696,960 filed May 8, 1991 (now U.S. Pat. No. 5,140,016), which is a continuation of Ser. No. 07/555,377 filed Jul. 19, 1990 (now U.S. Pat. No. 5,080,893); which is a continuation of Ser. No. 07/199,687 filed May 31, 1988 now abandoned.

BACKGROUND OF THE INVENTION

1. Field of the Invention

The present invention relates to the improvement of surgical techniques and tissue-protective surgical solutions.

2. Discussion of the Prior Art

Adhesions of the tissues and organ surfaces involved in surgery occasioned by manipulative trauma of the tissue surfaces during the surgery and other causes such as drying and ischemic trauma constitute one of the most serious post-operative complications of surgical procedures.

Although a variety of techniques have been proposed to reduce adhesions, the problem continues to plague the art and seriously compromise even the finest and most scrupulously performed surgeries. Prior attempts to alleviate the problem and the disappointing results attendant therewith are described by Davis et al, Surgery, Vol. 2, p. 87 (1937); Gozalez, Surgery, Vol. 26, p. 181 (1949); Hunter et al, J. Bone Joint Surg., Vol. 53A, p. 829 (1971); Ellis, Surg. Gynecol. Obst., Vol. 133, pp. 497–511 (1971); Lindsay et al, In Verdan, C. (ed.); Tendon Surgery of the Hand, Lond, Churchill Livingstone, pp. 35–39 (1979); Potenza, J. Bone Joint Surg., Vol. 45A, p. 1217 (1963); Verdan, J. Bone Joint Surg., Vol. 54A, p. 472 (1972); St. Onge et al, Clin. Orthop., Vol. 148, pp. 259—275 (1980); Thomas et al, Clin. Orthop., Vol. 206, pp. 281–289 (May, 1986); and Weiss et al, Bull. Hosp. Jt. Dis. Orthop. Inst., Vol. 46(1), pp. 9–15 (1986).

Goldberg et al [Arch. Surg., Vol. 115, pp. 776–780 (1980)] describe the use of certain hydrophilic polymer solutions (Povidone polyvinylpyrrolidone K-30 PVP and dextran) to coat tissue exposed to drying and/or manipulative peritoneal trauma, as well as the surgical articles, etc. which contact the tissue before and during surgery to prevent adhesions. Although the materials and methods of Goldberg et al showed some improvement over other research studies in which hydrophilic polymer solutions were used to attempt to reduce the incidence of surgical adhesions, there still exists a significant need for improvement.

A distinct disadvantage associated with the materials and methods of Goldberg et al and other prior art which has shown some benefit is the required use of highly concentrated solutions of the polymeric materials which makes practical use in surgery very difficult. Concentrated polymer solutions (greater than about 10–15%), for example, the 25% PVP and dextran solutions used by Goldberg et al, become sticky due to drying during surgery on the surfaces of tissue, surgeons' gloves, instruments, etc. This can seriously interfere with normal surgical procedures. High concentrations of PVP (K-30—molecular weight about 40,000) and dextran (molecular weight about 300,000) were required to achieve even some degree of tissue protection. Many studies prior to the report of Goldberg et al used lower concentrations of PVP, dextran or other water-soluble polymers which were even more ineffective. For example, Ellis [supra] stated that "use of PVP was accompanied by a slightly greater incidence of adhesions" in a rat peritoneal adhesions study. He also stated that because "such macromolecular solutions as plasma or dextran are known to be absorbed rapidly through functional lacunas on the under surface of the diaphragm . . . it is therefore probable that any effect of PVP or any other macromolecular solution introduced into the peritoneal cavity could only be transitory." In the study by Berquist et al [Eur. Surg. Res., Vol. 9, p. 321 (1977)] using 10% dextran-70 (molecular weight 70,000) and 1% hyaluronic acid (molecular weight unknown) as a post-coating at the completion of surgery, it was reported that there was "no difference between control and treated groups" for adhesions in rat and rabbit studies. Even attempts to use the relatively low molecular weight dextran-70 at very high concentrations (32%) based on suggestions of some beneficial effect in reducing genital tract adhesions in female rabbits [Neuwirth et al, Am. J. Obstet. Gynecol., Vol. 121, p. 420 (1974)] have not proven very successful. A commercial 32% (w/v) solution of dextran-70 was introduced as a hysteroscopy fluid about 1984, but recent studies have shown "no effect in reducing adhesions" using 32% dextran [Hadick et al, Military Medicine, Vol. 152, p. 144 (1987)].

Moreover, the use of such high concentrations may increase the expense of the surgical solutions and poses problems in preparing, purifying, stabilizing and storing solutions of such highly concentrated and often viscous solutions. For example, 32% dextran tends to crystallize "when subjected to temperature variations or when stored for long periods" [data sheet for commercial 32% dextran-70 solution].

Although the studies reported by Goldberg et al indicated some modest improvement in preventing adhesions using 25% PVP (molecular weight 40,000) and a slight improvement with 25% dextran (molecular weight 300,000) even using a surgical method involving coating of tissues and surgical implements before surgical manipulation, the materials and surgical solutions used were clearly impractical for clinical use in surgery.

In U.S. Pat. No. 5,080,893 (and in U.S. Pat. No. 5,140,016 and application Ser. No. 07/750,840 filed Aug. 29, 1991, supra), there are described improved methods, techniques and compositions for preventing surgical adhesions in surgery.

Surgical adhesions, however, are only one of the several types of complications which arise from the damage inflicted to tissue during surgical procedures. In addition to the formation of post-operative adhesions, tissue trauma during surgery can lead to a host of other potentially serious complications during and following surgical procedures, including:

(1) excessive blood vessel damage with increased bleeding during surgery and with greater risk of post-operative hemorrhage;

(2) enhancement of (acute) post-operative inflammation with prolongation of healing and damage to adjacent healthy tissues, as well as increased potential for chronic prolonged inflammation with associated secondary complications, pain, etc.;

(3) compromised wound healing with excessive scar tissue, of particular importance in orthopedic and plastic surgery;

(4) damage to organs and tissues which can result in impaired organ function, i.e., kidneys, liver, heart, lungs, etc.;

(5) blood vessel damage which can reduce blood supply with partial ischemia of muscle tissues and organs, leading to compromised function of muscle and vital organs, which is a life-threatening situation for heart muscle damage; and (6) increased susceptibility to acute and chronic 15infections due to preferential adherence and growth of pathogens on damaged tissue sites (post-operative staph and pseudomonas infections) with increased difficulty in treatment, slower recovery and greater chance of life-threatening systemic sepsis.

All of the above tissue damage related complications can result in longer hospitalization, patient discomfort, greater risk of morbidity and mortality, greater incidence of re-hospitalization and corrective surgery with associated patient risks, and higher health care costs.

Desiccation and abrasion tissue damage during surgery can lead to a variety of pathological surgical and postoperative complications. Damage due to desiccation and abrasion of the ovaries often results in formation of a thin fibrous membrane over the surface of the organ. Often this membrane is difficult to see with the unaided eye, yet it can act as a physical barrier to prevent transport of an egg to the Fallopian tube, thus preventing fertilization.

Prosthetic devices and implants such as heart valves, ventricular assists, vascular grafts, ligaments, tendons, corneas, skin grafts, muscle grafts, etc., which are derived entirely or in part from animal or human tissue or organs are subjected to handling and manipulation in the normal course of harvesting, processing, manufacturing, shipping and storage of prostheses. Some specific examples of such bioprostheses include, but are not limited to, porcine heart valves, fetal tissue derived vascular grafts (e.g., from umbilical tissue), fetal neurological tissue, electrically activated muscle blood pumps (e.g., ventricular assist devices), etc. The manipulation of these tissue derived bioprostheses and organ transplants can damage tissues, e.g., by desiccation or abrasive trauma, and thereby adversely affect in vivo biophysical or biochemical properties and reduce the safety and efficacy of the bioprosthesis or organ transplant. Organ and tissue transplants such as hearts, lungs, kidneys, livers, corneas, tendons, etc., can be similarly damaged by the normal manipulation that occurs with harvesting, storing, preparing, processing, shipping and implanting organs, tissues or composite bioprostheses into recipient patients.

It is an object of the present invention to provide improved compositions and methods for protecting tissue and preventing tissue damage in surgery.

It is another object of the present invention to provide improved methods and compositions for protecting human and animal derived tissues and organs during the manipulations that occur during harvesting, processing, storing, shipping and implantation thereof from trauma and damage which can result in impaired organ or tissue function or induce undesirable biological behavior.

Finally, it is an additional object of the present invention to provide improved compositions and methods for protecting those parts of bioprostheses derived from animal or human tissues or organs from trauma and damage during the harvesting thereof and the manufacture, processing, storing, manipulation, shipping and implantation of the bioprostheses, which trauma or damage could result in impaired bioprosthesis function or induce undesirable biological behavior.

SUMMARY OF THE INVENTION

The above and other objects are realized by the present invention, one embodiment of which is a method of protecting tissue and preventing tissue damage in surgery comprising providing surfaces involved in surgery with a wet coating of a physiologically acceptable aqueous solution of a hydrophilic, polymeric material prior to manipulation of the tissue during surgery, wherein:

A) the polymeric material is a water-soluble, biocompatible, pharmaceutically acceptable polypeptide, polysaccharide, excluding hyaluronic acid having a molecular weight above about 1,500,000, synthetic polymer, salt, complex or mixture thereof; and B) the polymeric material has a molecular weight of about 50,000 D or above, and the concentration of the aqueous solution of the polymer is in the range of from about 0.01% to about 15% by weight; the molecular weight and concentration having values such that the aqueous solution is capable of providing wet coatings on the tissue surfaces.

Another embodiment of the present invention is a method of protecting tissue and preventing tissue damage in surgery comprising providing surfaces involved in the surgery with a wet coating of a physiologically acceptable aqueous solution of a hydrophilic, polymeric material prior to manipulation of the tissue during surgery, wherein:

A) the polymeric material is a water-soluble, biocompatible, pharmaceutically acceptable, hyaluronic acid having a molecular weight above about 1,500,000, salt, complex or mixture thereof; and B) the concentration in the aqueous solution of the hyaluronic acid, complex or salt is in the range of from about 0.01% to less than about 1% by weight, the molecular weight and concentration having values such that the aqueous solution is capable of providing wet coatings on the tissue surface.

Yet another embodiment of the present invention comprises a surgical article, surfaces of which are adapted for contacting tissue surfaces during surgery having a coating thereon formed from one of the compositions described above.

A further embodiment of the present invention relates to a method of protecting from damage tissues or organs during the harvesting thereof from animals or humans, the manufacture therefrom of bioprostheses, and the subsequent manipulations and implantations of the bioprostheses in animals or humans, comprising providing the tissue or organ surfaces with a wet coating of a physiologically acceptable aqueous solution of a hydrophilic, polymer material prior to and during the harvesting, manufacture of bioprostheses, manipulations and implantations thereof, wherein:

A) the polymeric material is a water-soluble, biocompatible, pharmaceutically acceptable polypeptide, polysaccharide, excluding hyaluronic acid having a molecular weight above about 1,500,000, synthetic polymer, salt, complex or mixture thereof; and B) the polymeric material has a molecular weight of about 50,000 D or above, and the concentration in the aqueous solution of the polymer is in the range of from about 0.01% to about 15% by weight, the molecular weight and concentration having values such that the aqueous solution is capable of providing wet coatings on the surfaces.

A still further embodiment of the invention relates to the above-described coated bioprostheses.

A final embodiment of the invention comprises a method of protecting from damage tissues or organs or parts thereof during the harvesting thereof from animals or humans, the subsequent manipulations and implantations of the tissues or organs or parts thereof in animals or humans, comprising providing the tissue and organ surfaces with a wet coating of a physiologically acceptable aqueous solution of a hydrophilic, polymeric material prior to and during the harvesting, manipulations and implantations thereof, wherein:

A) the polymeric material is a water-soluble, biocompatible, pharmaceutically acceptable polypeptide, polysaccharide, excluding hyaluronic acid having a molecular weight above about 1,500,000, synthetic polymer, salt, complex or mixture thereof; and B) the polymeric material has a molecular weight of about 50,000 D or above, and the concentration in the aqueous solution of the polymer is in the range of from about 0.01% to about 15% by weight, the molecular weight and concentration having values such that the aqueous solution is capable of providing wet coatings on the surfaces.

DETAILED DESCRIPTION OF THE INVENTION

Figure 1:
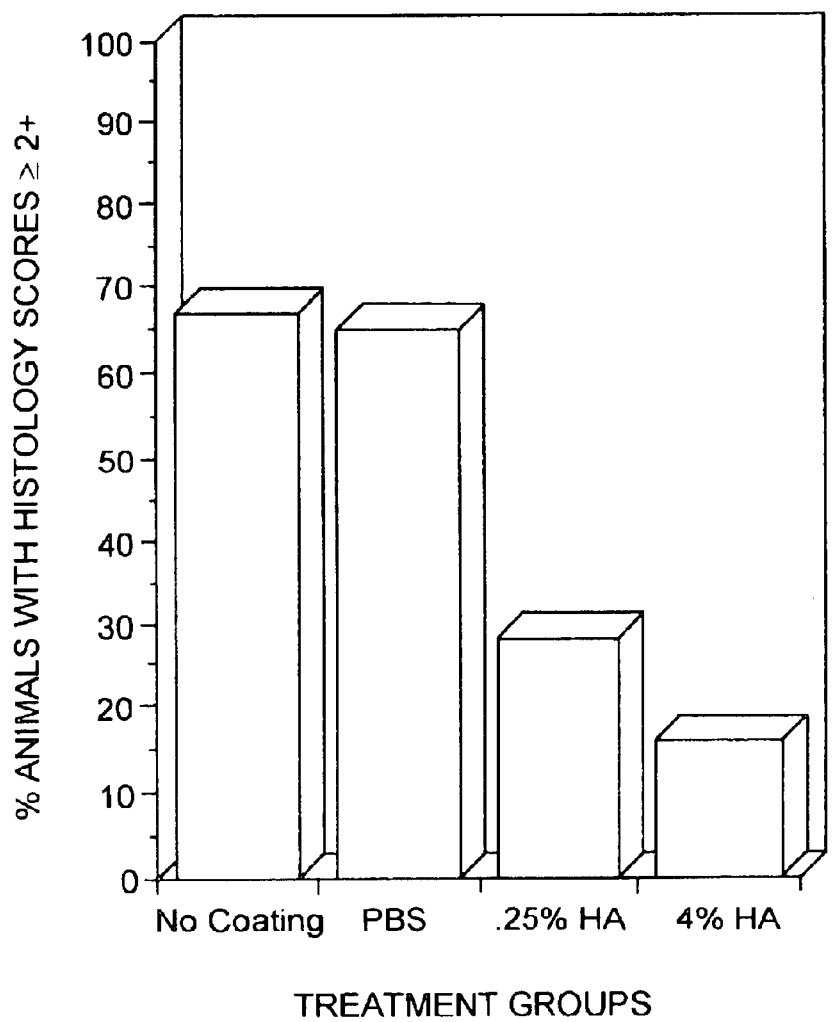
FIG. 1 is a graphical depiction showing the tissue protective qualities of the coating of the invention.

The present invention is predicated on the discovery that damage to tissue from surgical procedures may be prevented to a far greater extent than previously achieved by ensuring pre-coating of the involved tissues prior to the surgical manipulation or desiccation thereof or exposure to gases used in endoscopic procedures with the above-described solutions. Pre-coating of all surgical articles destined for contact with the involved tissues wherein the coating solution has the composition defined above is a further beneficial preferred embodiment of the invention.

The novel compositions of the invention unobviously reduce the incidence of tissue damage due to trauma and desiccation during surgical techniques to a far greater degree than would be expected from a reading of the extensive literature in this field.

It has been found, as demonstrated hereinbelow, that the use of hydrophilic polymer solutions in the molecular weight and concentration ranges described herein results in an unexpected significant decrease in the risk of tissue damage.

The unexpected benefit of using the polymer compositions of the invention with pre-coating of the involved tissue has been clearly shown to give far better results than post-operative or post-tissue manipulative treatment of the coating.

Furthermore, the surprisingly advantageous tissue-protective properties of the compositions of this invention have been demonstrated when used to coat tissue prior to surgical manipulation, even when conventional irrigating solutions are subsequently used during surgery.

For purposes of the present invention, the following definitions are applicable herein.

"Surfaces" refers to the surfaces of all tissue involved in and subject to manipulation by a foreign object during surgery or exposed to traumatic drying in the surgical field, as well as the surfaces of all surgical articles used in surgery and which may contact the involved tissue.

"Involved tissue surfaces" refers to all tissue involved in and subject to manipulation by a foreign object during surgery or exposed to traumatic drying in the surgical field.

The term "surgical articles" refers to all instruments, devices, implants, accessories, swabs, sponges, gauzes, gloves, sutures, etc., used in surgery and which may contact the "involved tissue."

"Surgery" refers to all invasive surgical techniques which expose "tissue" subject to surgical adhesions and tissue damage, including endoscopic procedures.

"Manipulation" refers to all possible traumatic exposure of "involved tissue," e.g., abrasion, dessication, etc., which can cause surgical adhesions and/or tissue damage.

The term "surgical adhesions" refers to the collagenous connective tissue which develops post-operatively after manipulative trauma to the "involved tissue." Also defined by this term are adhesions produced from "involved tissue" due to drying and/or ischemic trauma during the surgical procedure.

The term "tissue damage" refers to an insult to hard and soft tissues and organs that results in a temporary or permanent effect on the physical, cellular, physiological or biochemical state of the tissue such as discoloration due to desiccation or abrasive trauma, visual or microscopic damage to tissues or organs, including damage to mesothelial, epithelial or endothelial cells, changes in tissue mechanical properties, i.e., embrittlement due to drying and changes in metabolic function of surface cell layers, e.g., enzyme function.

The phrase "hydrophilic, polymeric material" refers to all pharmaceutically acceptable macromolecular materials, synthetic or natural, which are hydrophilic, biocompatible and non-toxic with respect to "involved tissue."

"Coating formed from the aqueous composition" refers to the "wet coating" formed on the coated surfaces using the aqueous composition, as well as coatings formed from the aqueous composition which are dried and may be subsequently re-wetted to produce the wet coating.

The term "prosthesis" refers to a device for replacing a part of the body of a human or animal.

The term "bioprosthesis" refers to a prosthesis composed at least in part from human or animal derived tissues or organs.

Molecular weights (Mw) reported are weight average molecular weights. Molecular weight may be determined by laser light scattering [Yu et al, in Zadisch, M. and Bose, A. (eds.); Harnessing Biotechnology for the 21st Century, Washington, D.C., Amer. Chem. Soc., pp. 80–84 (1992)].

Solution viscosities (centipoise) were measured at 25° C. using a Brookfield cone and plate viscometer.

In general, there is extensive literature on attempts to use various hydrophilic polymer solutions to prevent surgical adhesions by applying such solutions to the tissue surfaces in the surgical field following manipulative procedures and tissue trauma and just prior to wound closure. The concept guiding such studies has been that the viscous polymer solutions might afford a protective barrier to bridging of the traumatized tissues by collagenous connective tissue (adhesions). Polyvinylpyrrolidone (PVP), carboxymethylcellulose (CMC), dextran (dex) and hyaluronic acid (HA) have all been investigated, but no clinically practical results have been achieved.

The present invention is predicated on the discovery that a major improvement in tissue protection and prevention of damage to tissue generally is surprisingly achieved with aqueous hydrophilic polymer solutions of high molecular weight (>50,000 D) using a method of tissue protection involving the application of the polymer solution to the tissue before drying or surgical manipulative procedures are initiated. This combination of materials and method of use results in uniquely successful tissue protection in general, as well as prevention of surgical adhesions, and overcomes the drawbacks associated with the prior art wherein either (1) the polymers used (i.e., PVP or dextran) have been of molecular weights less than 500,000, necessitating high concentrations (>20%) to have any beneficial effect and, therefore, exhibiting difficult sticky physical handling properties during surgery, and/or (2) the solutions have been used by a method involving coating of tissues at the conclusion of surgery, thus not affording the tissue protection during surgery which is provided by the method of the present invention. Thus, by the combined use of (a) more dilute aqueous hydrophilic polymer solutions made possible with polymers having molecular weights greater than 50,000 D and concentrations to provide sufficient viscosity to protect tissue surfaces, and (b) a method of use wherein the solution is used as a tissue protective coating at the beginning of surgery and periodically during surgery, it has been discovered that a major improvement in preventing tissue damage which is clinically practical, is achieved.

Although in theory, virtually any biocompatible, water-soluble polymer (e.g., polysaccharides, polypeptides, carbohydrates, synthetic polymers and their salts) having a molecular weight >50,000 D and concentration to provide sufficient viscosity to protect tissue surfaces may be used to produce the tissue-protective aqueous solutions of the present invention, polyvinylpyrrolidone (PVP), carboxymethylcellulose (CMC) and hyaluronic acid (HA) and its salts are particularly effective. However, because HA is a natural constituent of extracellular matrix and tissues, exhibits biocompatibility and is effective at low concentrations, HA solutions represent a preferred embodiment of this invention.

Polyvinylpyrrolidones reported in attempts to reduce adhesions heretofore (i.e., K-30 or K-40) have been of molecular weights substantially less than 500,000 and have been ineffective at lower concentrations (<20%) or sticky and impractical at higher concentrations where some benefit has been reported.

The PVP materials of this invention have substantially greater weight average (Mw) or viscosity average (Mv) molecular weights than 500,000. These include K-90 PVP (having a reported Mw or Mv molecular weight of about 1,000,000) or high molecular weight PVP made by gamma radiation polymerization of N-vinylpyrrolidone (gamma-PVP). Although high Mv PVP such as K-90 may be used in the method of the present invention at concentrations of 10–15%, it is preferred to use gamma-PVP which may be prepared with Mv substantially greater than 1,000,000 (to Mv of 5,000,000 or more). Gamma-PVP of extremely high Mv is advantageous in that it may provide solutions of sufficient viscosity to protect tissue surfaces involved in surgery at concentrations of 5% or less. Various bio-acceptable PVP and gamma-PVP copolymers may also be used in the practice of the invention. Furthermore, other highly purified bio-acceptable, high molecular weight, synthetic hydrophilic polymers, e.g., polyethylene glycol, dimethylacrylamide and their copolymers, etc., may be used in this invention. It is also within the scope of this invention to utilize gamma-PVP which is prepared in combination with the other synthetic polymers, proteins or polysaccharides mentioned hereinabove.

The carboxymethylcellulose (CMC) useful in combination with the novel method of use in this invention are also of molecular weights greater than 500,000 and concentration to provide sufficient viscosity to protect tissue surfaces from damage and to prevent adhesions. A preferred example is a commercially available CMC of about 800,000 molecular weight. Such polyelectrolyte polysaccharides are especially valuable because of the good viscoelastic behavior of aqueous solutions which enable the use of lower solution concentrations at high molecular weights for effective tissue protection; aqueous solutions with concentrations of 1–2% or less by the method proposed herein.

Naturally occurring polysaccharides which occur in cartilage, soft tissue and cell membranes such as hyaluronic acid (HA) and its salts are especially effective as tissue-protective adhesion preventing agents using the method of the present invention. Although naturally occurring HA with a molecular weight greater than 1,000,000 has been used clinically in ophthalmic surgery to maintain the anterior chamber, such solutions require HA concentrations of 1.0% or more and, because of their extremely high viscosity, are not readily applied as tissue-protective solutions according to the method of this invention. As either or both HA molecular weight and concentration increase, the viscosity of the solution likewise increases. It has been discovered that the ability of HA solutions to prevent tissue damage and reduce adhesion formation is related to the viscosity, not just molecular weight or concentration, of the solution. Additionally, due to the high cost of highly concentrated ophthalmic HA formulations, it has been impractical to consider any surgical application involving more than 1–2 ml of a 1% solution. Unexpectedly, we have discovered that dilute HA solutions with molecular weights >500,000 are highly effective at concentrations of 0.01% to 1.0% by weight when used for tissue damage prevention by the method of the present invention. Such dilute HA solutions, therefore, represent uniquely efficient materials for the method of the invention because of the excellent biocompatibility, favorable non-Newtonian rheology and tissue coating by very dilute solutions, practical cost for general surgical applications which may require 1–2 liters of the dilute solutions and exceptional tissue protective qualities when combined with the method of use according to the invention. As indicated in the following examples, even a 0.25% solution of about 1,500,000 molecular weight HA effectively prevents tissue damage arising from surgery.

Virtually all types of surgery in which post-operative complications arising from tissue damage during surgery (e.g., peritoneal, pericardial, obstetric, gynecological, neurological, arthroscopic, laparoscopic, endoscopic, orthopedic, plastic, reconstructive, prosthetic, ENT, dental, muscle or tendon) and surgical procedures performed endoscopically, are susceptible to modification and improvement according to the present invention, as well as the so-called "least-invasive-surgery" (LIS) or "minimally invasive surgery" (MIS) microsurgical procedures. Additional procedures which often give rise to tissue damage cause by adverse drying and anoxia are those which entail the use of carbon dioxide. Important examples include abdominal, thoracic, cardiovascular, ob/gyn and neuro-surgical procedures, all of which are fraught with potentially severe post-operative complications which may be attributed to surgical trauma. In the case of cardiac surgery involving transplants, vascular repair and by-passes, valve replacements, etc., reoperations continue to increase every year with repeat coronary artery surgery comprising the majority of such reoperations. Post-operative pericardial tissue damage complications from initial surgery are common and subject patients undergoing repeat cardiac surgery to substantial risks. Potential injury to the heart, great vessels and extracardiac grafts during resternotomy, as well as prolonged operative time, increase morbidity and mortality. Resternotomy is associated with as much as a 6% incidence of major vascular injury and a more than 35% mortality has been reported for patients experiencing major hemorrhage during resternotomy. A 50% mortality has been reported for associated injuries to aortocoronary grafts. Pediatric cardiac surgery is also associated with a very high incidence of reoperations. In view of the marked increase in cardiac surgery and reoperations and the potentially serious complications related to complications arising from tissue damage during pericardial surgery, prevention of such tissue damage represents a major health care need.

Peritoneal complications represent another major health care problem with potentially serious post-operative complications associated with all types of abdominal surgery, with a reported incidence of 50–90% for laparotomies. A dramatic reduction in abdominal tissue damage complications is made possible and clinically practical by the use of the materials and method of the present invention.

Histology studies were carried out in rats to test the hypothesis that coating tissue surfaces with hyaluronic acid solution prior to exposing said tissue to a physical insult could prevent damage to surgically involved organs. Controlled desiccation and abrasion were employed to induce damage to the cecum of rats. Results showed that a tissue protective coating of hyaluronic acid reduced serosal damage caused by these surgical procedures. In another study, the abdominal organs of three groups of rats were treated with either an HA solution, phosphate buffered saline (PBS) or no solution. The cecum of each animal was abraded in a standardized manner and the degree of trauma to the cecum determined histologically. The study was conducted in a random/blind fashion. The results showed that the HA solution significantly reduced serosal pathology compared to the non-coated and PBS-coated groups. These studies confirm the hypothesis that HA and other viscoelastic polymer solutions of sufficient viscosity, as determined by molecular weight and concentration, provide a protective barrier to tissues and organs, thereby preventing surgical tissue damage.

EXAMPLE 1

Female Sprague-Dawley rats (225–250 gm) were used in all experiments using a random/blind protocol. Animals were anesthetized by an intramuscular injection of ketamine (100 mg/kg body weight) and xylazine (10 mg/kg body weight). The abdominal cavity of each animal was exposed by a mid-ventral incision (3–4 cm). Following laparotomy, 2 ml of test solution was placed in the abdominal cavity and then gently distributed to coat the organs. The cecum was located with cotton swabs and placed on a sterile Teflon sheet. One ml of test solution was placed over the dorsal surface of the cecum and another 1 ml placed over the ventral surface. The cecum was treated according to the desiccation procedure (see following section) or abrasion procedure (see following section). The cecum was then placed back in the abdominal cavity and the abdomen closed with 4-0 nylon suture. The animals were sacrificed two days post-operatively and their ceca evaluated histologically.

Cecal Desiccation Procedure

A desiccation apparatus was developed to induce a reproducible degree of tissue drying. Compressed air was connected to an air flow meter, a desiccant reservoir and a 0.22 $\mu$m nylon filter. The filter was placed downstream from the desiccant to remove particulates and potential infective agents. Air flowed to an 8 cm diameter cone placed 2 cm above the cecum which was exposed for five minutes to an air flow of 30 ml/min.

Cecal Abrasion Procedure

A constant force rotary abrader was used with an abrading surface of Type VII surgical gauze (1.77 $cm^2$ surface area) secured to the fixed force rotating shaft by a rubber septum. During the abrading procedure, the cecum was secured by a Teflon device that contained a hole large enough to accommodate the abrading surface. Abrasion conditions were as follows: 70 gm abrasion force, 60 revolutions of the spline shaft, abrasion of two sites on the ventral surfaces of the cecum, 1.5 cm diameter abrasion surface (Type VII surgical gauze).

Further experimental data and results were as follows. Animals were sacrificed two days following surgery. The abdominal cavity was accessed via a left paramedian incision (approximately 6 cm in length) through the skin and peritoneum. The cecum was removed and placed overnight in 10% Bouin's solution. Following fixation, two sections were removed from the cecum and the tissue embedded in paraffin, sectioned and stained with hemotoloxyin and eosin. Tissue pathology was graded blindly on a 0 to 3+ scale (see Table 1). The dorsal surface of each cecum served as a non-abraded control to ensure that handling of the cecum during the abrasion procedure did not cause significant damage. The results are set forth in Tables 2–4. See also FIG. 1.

TABLE 1

Histology Grading Scale For Evaluation Of Cecal Trauma

| | |
|---|---|
| 0 = | Serosa is normal in appearance. |
| +/− = | Very mild hypertrophy of mesothelium. |
| 1+ = | Hypertrophy of mesothelium with mild infiltration of mononuclear inflammatory cells beneath the serosa. The serosa may be mildly thickened. |
| 2+ = | Significant hypertrophy of mesothelium with moderate infiltration of mononuclear inflammatory cells. The serosa is moderately thickened due to inflammation. |
| 3+ = | Extensive hypertrophy of mesothelium with significant infiltration of mononuclear inflammatory cells. The serosa is significantly thickened due to inflammation. A fibrous exudate may be present above the mesothelium. |

TABLE 2

Effect Of Hyaluronic Acid Solutions On Prevention Of Tissue Trauma Caused By Desiccation — Study A

| Group (N = 5/Group) | Treatment | % Animals with Scores ≧ 2 |
|---|---|---|
| I | no desiccation/no treatment | 0 (0/5) |
| II | no solution coating | 100 (5/5) |
| III | lactated Ringer's | 100 (4/4) |
| IV | 4 mg/ml hyaluronic acid | 20 (1/5) |

TABLE 3

Effect Of Hyaluronic Acid Solutions
On Tissue Protection In
Cecal Abrasion Model — Study B

| Group (N = 5/Group) | Treatment | % Animals with Scores ≧ 2 |
|---|---|---|
| I | phosphate buffered saline | 80 (4/5) |
| II | 4 mg/ml hyaluronic acid | 20 (1/5) |
| III | phosphate buffered saline | 100 (5/5) |
| IV | 4 mg/ml hyaluronic acid | 40 (2/5) |

TABLE 4

Effect Of Hyaluronic Acid Solutions
On Prevention Of Tissue Trauma In
Rat Cecal Abrasion Model — Study C

| Group (N = 24–26/Group) | Treatment | % Animals with Scores ≧ 2 |
|---|---|---|
| I | no coating | 67 (16/24) |
| II | phosphate buffered saline | 65 (17/26) |
| III | 2.5 mg/ml hyaluronic acid | 28 (7/25) |
| IV | 4 mg/ml hyaluronic acid | 16 (4/25) |

Desiccation experiments showed that the serosa of the cecum was damaged by excessive drying consistent with findings of Ryan et al [Am. J. Path., Vol. 65, pp. 117–140 (1971)]. Results showed that lactated Ringer's solution did not reduce damage caused by desiccation (Table 2). Ryan has reported that, in fact, desiccation in the presence of saline induces more damage to the serosa than desiccation alone. Standard surgical irrigation solutions, therefore, do not offer tissue protection.

The 4 mg/ml HA solution group clearly showed reduced desiccation damage to the serosa, i.e., tissue protection against desiccation trauma. Cecal abrasion studies also clearly demonstrated that HA solutions, used as a tissue pre-coating, acted to protect tissues from abrasion damage. The desiccation and abrasion of cecal tissue represent real occurrences in normal surgical procedures that very likely cause post-operative adhesion formation, as well as effect numerous other surgical and post-operative complications.

The hydrophilic, polymeric material may be dissolved in any suitable aqueous solution conventionally employed in surgery, e.g., Ringer's lactate, normal saline or any other iso-osmolar physiological medium.

EXAMPLE 2

Protection of Porcine Heart Valves

Prior to harvesting of pig heart valves, tissues in the surgical excision field are coated with 50–100 ml of aqueous sodium hyaluronate solution having a viscosity of 95 centipoise at 100 sec$^{-1}$. The excised heart valves are fixed according to normal aldehyde fixation procedures and are maintained in or are coated with the HA solution during handling and manufacturing procedures, especially during trimming, suturing, quality assurance examinations and preparation for packaging, which normally involve conditions of drying and abrasive manipulative damage to the tissues. The use of the solutions substantially inhibit this tissue trauma, and thereby helps maintain the maximal desired physico-chemical properties of the tissue and the fragile leaflet valve structure and function. This is achieved by maintaining the tissue protective environment during handling which is afforded by the above solutions.

EXAMPLE 3

Protection of Umbilical Cord Tissue for Small Diameter Vascular Grafts

Fetal tissue is maintained in a moist condition following expression by immersion in the NaHA solution of Example 2. Following normal washing and fixative treatment, handling, cutting and other manufacturing procedures are conducted with tissue coated with the NaHA solution to inhibit desiccation and manipulative tissue damage. The resulting small diameter graft prostheses (less than 6–7 mm) exhibit superior physical and biological properties as compared with vascular prostheses which have been damaged by normal handling methods in general use.

We claim:

1. A method of protecting tissue and prevention tissue damage in surgery comprising providing surfaces involved in said surgery with a wet coating of a physiologically acceptable aqueous solution of a hydrophilic, polymeric material prior to manipulation of said tissue during said surgery, wherein:
   A) said polymeric material is a water-soluble, biocompatible, pharmaceutically acceptable polypeptide; polysaccharide, excluding hyaluronic acid having a molecular weight above about 1,500,000; synthetic polymer; or a salt complex or mixture thereof; and
   B) said polymeric material has a molecular weight of about 50,000 D or above, and the concentration in said aqueous solution of said polymer is in the range of from about 0.01% to about 15% by weight, said molecular weight and concentration having values such that said aqueous solution is capable of providing wet coatings on said surfaces involved in said surgery.

2. The method of claim 1 wherein said polymeric material is carboxymethylcellulose, PVP, hyaluronic acid, pharmaceutically acceptable salts or complexes thereof or mixtures thereof.

3. The method of claim 2 wherein said polymeric material is carboxymethylcellulose or a pharmaceutically acceptable salt or complex thereof.

4. The method of claim 2 wherein said polymeric material is PVP or a pharmaceutically acceptable salt or complex thereof.

5. The method of claim 2 wherein said polymeric material is hyaluronic acid or a pharmaceutically acceptable salt or complex thereof.

6. The method of claim 1 wherein said surgery is abdominal, peritoneal, pericardial, obstetric, gynecological, neurosurgical, arthroscopic, laparoscopic, endoscopic, orthopedic, plastic, reconstructive, prosthetic, ENT, dental, muscle or tendon.

7. The method of claim 1 wherein said involved surfaces coated with said solution of polymeric material comprise tissue or surgical article surfaces or both.

8. A method of protecting tissue and preventing tissue damage in surgery comprising providing surfaces involved in said surgery with a wet coating of a physiologically acceptable aqueous solution of a hydrophilic, polymeric material prior to manipulation of said tissue during said surgery, wherein:
   A) said polymeric material is a water-soluble, biocompatible, pharmaceutically acceptable hyaluronic acid having a molecular weight above about 1,500,000, salt, complex or mixture thereof; and B) the concentration in said aqueous solution of said hyaluronic acid, salt or complex is in the range of from about 0.01% to less than about 1% by weight, said molecular weight and concentration having values such that said aqueous solution is capable of providing wet coatings on said surfaces involved in said surgery.

9. The method of claim 8 wherein said surgery is abdominal, peritoneal, pericardial, obstetric, gynecological, neurosurgical, arthroscopic, laparoscopic, endoscopic, orthopedic, plastic, reconstructive, prosthetic, ENT, dental, muscle or tendon.

10. The method of claim 8 wherein said involved surfaces coated with said solution of polymeric material comprise tissue or surgical article surfaces or both.

11. A Surgical article having surfaces adapted for contacting tissue surfaces during surgery, said surfaces of said surgical article having a wet coating thereon, said wet coating comprising a physiologically acceptable aqueous solution of a hydrophilic, polymeric material wherein:
   A) said polymeric material is a water-soluble, biocompatible, pharmaceutically acceptable polypeptide; polysaccharide, excluding hyaluronic acid having a molecular weight above about 1,500,000; synthetic polymer; or a salt, complex or mixture thereof; and
   B) a molecular weight of about 50,000 D or above, and the concentration in said aqueous solution of said polymer is in the range of from about 0.01% to about 15% by weight, said molecular weight and concentration having values such that said aqueous solution is capable of providing wet coatings on said surfaces; or a physiologically acceptable aqueous solution of a hydrophilic, polymeric material, wherein:
      I) said polymeric material is a water-soluble, biocompatible, pharmaceutically acceptable hyaluronic acid having a molecular weight above about 1,500,000, salt, complex or mixture thereof; and
      II) the concentration in said aqueous solution of said hyaluronic acid, salt or complex is in the range of from about 0.01% to less than about 1% by weight, said molecular weight and concentration having values such that said aqueous solution is capable of providing wet coatings on said surfaces.

12. A method of protecting from damage tissues or organs during harvesting thereof from animals or humans, manufacture therefrom of bioprostheses and subsequent manipulations and implantations of said bioprostheses in animals or humans, comprising providing said tissue or organ surfaces with a wet coating of a physiologically acceptable aqueous solution of a hydrophilic, polymeric material prior to and during said harvesting, manufacture of bioprostheses, manipulations and implantations thereof, wherein:
   A) said polymeric material is a water-soluble, biocompatible, pharmaceutically acceptable, polysaccharide, excluding hyaluronic acid having a molecular weight above about 1,500,000 polypeptide, synthetic polymer, salt, complex or mixture thereof; and
   B) said polymeric material has a molecular weight of about 50,000 D or above, and the concentration in said aqueous solution of said polymer is the range of from about 0.01% to about 15% by weight, said molecular weight and concentration having values such that said aqueous solution is capable of providing wet coatings on said surfaces.

13. A bioprosthesis comprised at least in part of tissue or an organ or part thereof of an animal or human, said tissue or organ or part thereof having a coating thereon of a physiologically acceptable aqueous solution of a hydrophilic, polymer material to protect said tissue or organ or part thereof from damage arising during harvesting thereof from said animal or human, manufacture of said bioprosthesis and manipulations and implantations of said bioprosthesis in animals or humans, wherein:
   A) said polymeric material is a water-soluble, biocompatible, pharmaceutically acceptable, polysaccharide, excluding hyaluronic acid having a molecular weight above about 1,500,000 polypeptide, synthetic polymer, salt, complex or mixture thereof; and
   B) said polymeric material has a molecular weight of about 50,000 D or above, and the concentration in said aqueous solution of said polymer is in the range of from about 0.01% to about 15% by weight, said molecular weight and concentration having values such that said aqueous solution is capable of providing wet coatings on said surfaces.

14. A method of protecting from damage tissues or organs or parts thereof during harvesting thereof from animals or humans, subsequent manipulations and implantations of said tissues or organs or parts thereof in animals or humans, comprising providing said tissue and organ surfaces with a wet coating of a physiologically acceptable aqueous solution of a hydrophilic, polymeric material prior to and during said harvesting, manipulations and implantations thereof, wherein:
   A) said polymeric material is a water-soluble, biocompatible, pharmaceutically acceptable polypeptide; polysaccharide, excluding hyaluronic acid having a molecular weight above about 1,500,000; synthetic polymer; or a salt, complex or mixture thereof; and
   B) said polymeric material has a molecular weight of about 50,000 D or above, and the concentration in said aqueous solution of said polymer is in the range of from about 0.01% to about 15% by weight, said molecular weight and concentration having values such that said aqueous solution is capable of providing wet coatings on said surfaces.

* * * * *

UNITED STATES PATENT AND TRADEMARK OFFICE
CERTIFICATE OF CORRECTION

PATENT NO. : 6,706,780 B2
DATED : March 16, 2004
INVENTOR(S) : Eugene P. Goldberg et al.

It is certified that error appears in the above-identified patent and that said Letters Patent is hereby corrected as shown below:

Column 12,
Line 18, change "prevention" to -- preventing --.
Line 27, after "polysaccharide" insert -- synthetic polymer and salts and complexes thereof and mixtures thereof, wherein said polysaccharide --.
Line 27, replace "excluding" with -- excludes --.
Lines 28 and 29, delete "synthetic polymer; or a salt complex or mixture thereof;".
Line 67, delete "salt, complex".

Column 13,
Line 21, after "polysaccharide" insert -- synthetic polymer and salts and complexes thereof and mixtures thereof, wherein said polysaccharide --.
Line 21, replace "excluding" with -- excludes --.
Lines 22 and 23, delete "synthetic polymer; or a salt, complex or mixture thereof;"
Line 34, after "acid" insert-- salt or complex thereof --.
Line 34, delete "about"
Line 35, delete "salt, complex".
Line 51, after "acceptable" insert --polypeptide--.
Line 52, after "polysaccharide," insert -- synthetic polymer and salts and complexes thereof, and mixtures thereof wherein said polysaccharide --.
Line 52, replace "excluding" with -- excludes --.
Lines 53 and 54, delete "polypeptide, synthetic polymer, salt complex or mixture thereof'.

UNITED STATES PATENT AND TRADEMARK OFFICE
CERTIFICATE OF CORRECTION

PATENT NO.    : 6,706,780 B2
DATED         : March 16, 2004
INVENTOR(S)   : Eugene P. Goldberg et al.

It is certified that error appears in the above-identified patent and that said Letters Patent is hereby corrected as shown below:

<u>Column 14,</u>
Line 3, after the phrase "said polymer is" insert -- in --.
Line 19, after "acceptable" insert -- polypeptide --.
Line 20, after "polysaccharide" insert -- synthetic polymer and salts and complexes thereof and mixtures thereof, wherein said polysaccharide --.
Line 20, replace "excluding" with -- excludes --.
Lines 45 and 46, delete "synthetic polymer; or a salt, complex or mixture thereof;".

Signed and Sealed this

Twenty-second Day of March, 2005

JON W. DUDAS
*Director of the United States Patent and Trademark Office*